Oct. 13, 1936. C. MALLERIN Plant Pat. 202
ROSE
Filed March 23, 1936
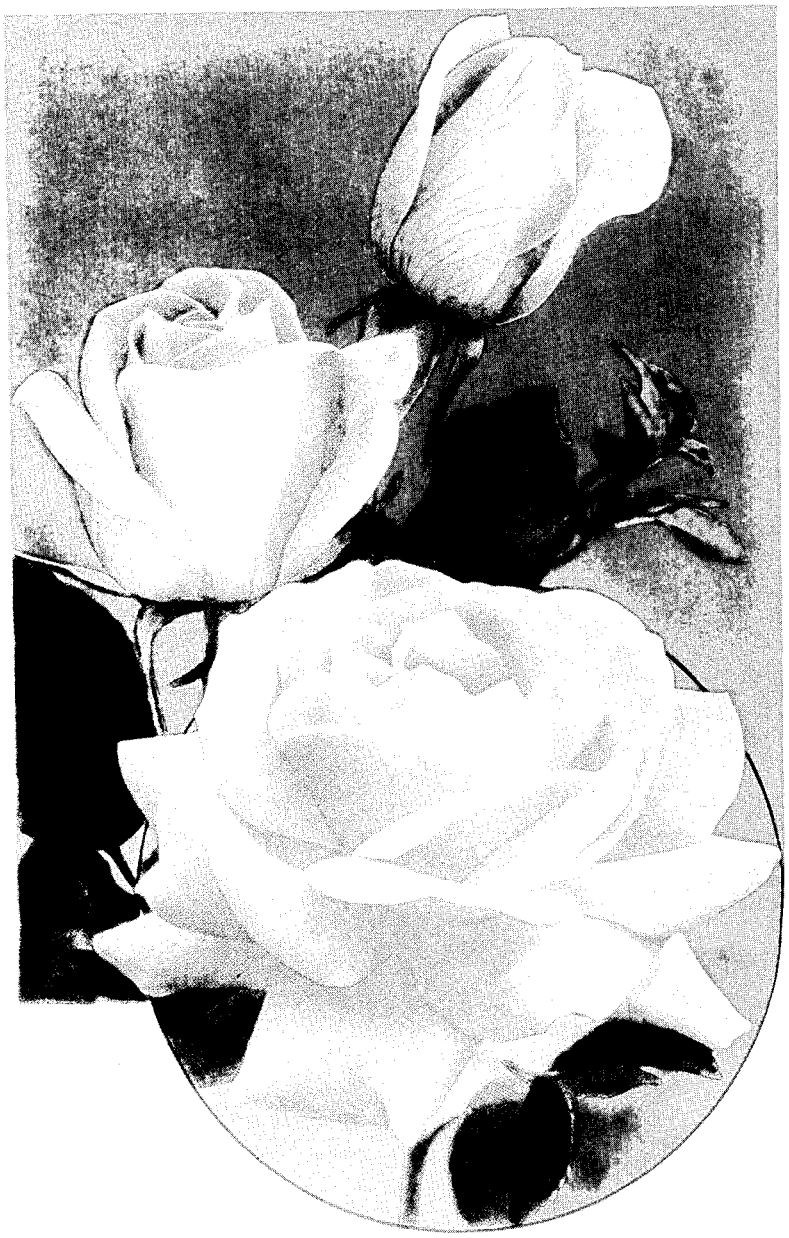
Inventor
C. Mallerin
By Robb & Robb
Attorneys Patented Oct. 13, 1936

UNITED STATES PATENT OFFICE

202

ROSE

Charles Mallerin, Varces, France, assignor to Jackson & Perkins Company, Newark, N. Y.

Application March 23, 1936, Serial No. 70,513

1 Claim. (Cl. 47—61)

The present invention relates to a new and distinct variety of "Rose" plant, having as its primary objective to further improve the yellow rose, including a reduction of the weaknesses inherent in the Pernetiana race, reinforcement and purification of the color by elimination of foreign tints.

The various operations culminating in this invention started by pollinating Ophelia with Souvenir de Claudius Pernet. These two parents were selected because Ophelia was and still is one of the most artistic buds we have in roses and at the same time one of the healthiest plants. Souvenir de Claudius Pernet is the purest yellow color and the strongest yellow parent genetically. One seedling of this cross was selected, the pollen of which was put back into Ophelia and one of the progeny of this new cross became the rose now in commerce under the name of Mrs. Pierre S. du Pont.

Mrs. Pierre S. du Pont has all the attributes of a good garden rose as to plant, health of foliage and floriferousness but the individual flowers leave much to be desired in form, lasting quality, clearness and purity of color. To correct these faults, I selected the pollen of Souvenir de Claudius Pernet which has an excellent form, color long lasting and of the purest yellow. I made this cross for several years in succession and in sufficient quantity to raise a large number of seedlings. After a long process of elimination, three seedlings remained for extensive tests in various parts of Europe and America, and the rose herein described was unanimously selected as the best of the three.

I may also add that my work toward a perfect yellow rose started in 1920 when the original cross of Ophelia and Souvenir de Claudius Pernet was made, and the present rose is the attainment of the objective. The rose has been asexually propagated for several years and comes uniformly true to form.

The following is a detailed description of this new variety, reference to color according with the Gravereaux color chart except where obviously the ordinary dictionary definition is meant:—

Parentage:
*Seed parent.*—"Mrs. Pierre S. du Pont."
*Pollen parent.*—"Souvenir de Claudius Pernet."

Classification:
Hybrid of Pernetiana.
*Commercial.*—Hybrid Tea (American Rose Society).

*Flower*

Blooming habit:
*Blooms.*—Profusely.
*Recurrent.*—Continuous.

Bud:
*Size.*—Very large.
*Form.*—Long, pointed. Unaffected by wet or hot weather.
*Color*—
*When sepals first divide.*—Saffron.
*When petals begin to unfurl.*—Saffron.
*When half blown:*
*Inside of petals.*—Saffron.
*Reverse of petals.*—Saffron.
*Sepals.*—Smooth edge; curl back when bud begins to open.
*Calyx*—
*Shape.*—Funnel.
*Size.*—Large.
*Aspect.*—Smooth.
*Peduncle*—
*Length.*—Long.
*Aspect.*—Rough.
*Color.*—Medium green, bronzy on sunny side.
*Strength.*—Erect, heavy.
*Opening.*—Opens well and is not affected by adverse conditions.

Bloom:
*Size.*—Large; average size when fully expanded 4".
*Borne.*—Singly.
*Stems.*—Long, strong.
*Form.*—When first open, globular. Permanence, retains its form to the end.
*Petalage.*—Double (full but open center). Number of petals under normal conditions 35 to 40.
*Color.*—Saffron—The color is homogeneous in all parts with hardly any variation at all.
*Discoloration.*—General tonality at end of
*First day*—Saffron.
*Second day*—Saffron.
*Third day*—Slightly paler.

Petals:
*Texture.*—Thick; unaffected by wet or hot weather.
*Appearance*—
*Inside.*—Velvety.
*Outside.*—Shiny.
*Form.*—Round.
*Arrangement.*—Imbricated (regularly arranged shingle-like.) Petaloids in center few and small.
*Persistence.*—Drop off clearly.
*Fragrance.*—Moderate.
*Nature.*—Fruity (Russet apple.)
*Lasting quality.*—On the plant very long; as cut flowers, long.

Genital organs:
*Stamens, anthers.*—Large, many.
*Color.*—Yellow.
*Arrangement.*—Regular around styles.
*Stamens, filaments (threads).*—Medium.
*Color.*—White.
*Pollen.*—Lemon yellow.

*Styles.*—Loosely separated, uneven length, medium, heavy.
*Stigmas.*—White.
*Ovaries.*—All enclosed in calyx.
Fruit:
Variety is fertile with its own pollen.
*Form.*—Ovoid, flat headed.
*Aspect.*—Smooth.
*Color at maturity.*—Russet brown.
*Sepals.*—Caducous (soon falling).

*Plant*

Form:
Bush of very harmonious form, all branches being of even length.
Growth:
Vigorous, branching.
Foliage:
Generally five leaflets.
*Size.*—Large.
*Quantity.*—Abundant.
*Color:*
*New foliage*—
*Upper side.*—Bronzy.
*Under side.*—Green and bronzy.
*Old foliage*—
*Upper side.*—Normal green.
*Under side.*—Lighter green.
*Shape.*—Oval pointed.
*Texture*—
*Upper side.*—Smooth.
*Under side.*—Rough.
*Ribs and veins.*—Ordinary.
*Edge.*—Serrated (saw toothed).
*Serration.*—Single, small.
*Rachis.*—Color, reddish.
Under side prickles.
*Stipules.*—Medium length, smooth.
*Disease resistance.*—Resistant.
Wood:
*New wood*—
*Color.*—Reddish.
*Bark.*—Smooth.
*Old wood*—
*Color.*—Green.
*Bark.*—Smooth.
Thorns (divided into thorns, prickles, and short needles):
*Thorns:*
*Quantity.*—On main stalks from base, ordinary; on laterals from stalks, few.
*Form.*—Broad base, medium length, hooked downward.
*Color when young.*—Green and red.
*Position.*—Irregular.
*Prickles:*
*Quantity.*—On main stalks, few; on laterals, none.
*Short Needles:*
*Quantity.*—On main stalks, none; on laterals, none.

I claim:—

A new and distinct variety of rose plant, characterized by its robust healthy growth, its perfection of form, the profuse blooming habit, and the lasting yellow color of uniform tint of its blossoms, substantially as shown and described.

CHARLES MALLERIN.